(12) United States Patent
Leporq et al.

(10) Patent No.: US 10,646,134 B2
(45) Date of Patent: *May 12, 2020

(54) METHOD FOR FAT CHARACTERIZATION USING MRI IMAGES ACQUIRED USING A MULTIPLE GRADIENT-ECHO SEQUENCE WITH BIPOLAR GRADIENTS

(71) Applicants: Institut National de la Sante et de la Recherche Medicale (INSERM), Paris (FR); Universite Paris Diderot—Paris 7, Paris (FR); Assistance Publique-Hopitaux de Paris, Paris (FR); Univesite de Versailles Saint-Quentin-en-Yvelines, Versailles (FR)

(72) Inventors: Benjamin Leporq, Clichy (FR); Simon Lambert, Villeurbanne (FR); Bernard Van Beers, Paris (FR)

(73) Assignees: INSTITUT NATIONAL DE LA SANTE ET DE LA RECHERCHE MEDICALE (INSERM), Paris (FR); UNIVERSITE PARIS DIDEROT—PARIS 7, Paris (FR); UNIVERSITE VERSAILLES SAINT-QUENTIN-EN-YVELINES, Versailles (FR); ASSISTANCE PUBLIQUE-HOPITAUX DE PARIS (APHP), Paris (FR)

( * ) Notice: Subject to any disclaimer, the term of this patent is extended or adjusted under 35 U.S.C. 154(b) by 209 days.

This patent is subject to a terminal disclaimer.

(21) Appl. No.: 15/568,839

(22) PCT Filed: Apr. 22, 2016

(86) PCT No.: PCT/EP2016/059099
§ 371 (c)(1),
(2) Date: Oct. 24, 2017

(87) PCT Pub. No.: WO2016/170168
PCT Pub. Date: Oct. 27, 2016

(65) Prior Publication Data
US 2018/0098711 A1   Apr. 12, 2018

(30) Foreign Application Priority Data

Apr. 24, 2015  (EP) .................................. 15305628

(51) Int. Cl.
*A61B 5/055*   (2006.01)
*G01R 33/48*   (2006.01)
(Continued)

(52) U.S. Cl.
CPC ............ *A61B 5/055* (2013.01); *A61B 5/4872* (2013.01); *G01R 33/4828* (2013.01);
(Continued)

(58) Field of Classification Search
None
See application file for complete search history.

(56) References Cited

U.S. PATENT DOCUMENTS

2004/0032977 A1 * 2/2004 Blezek ............... G01R 33/4828
                                                    382/128
2011/0044524 A1 * 2/2011 Wang .................... G01R 33/54
                                                    382/131
(Continued)

FOREIGN PATENT DOCUMENTS

WO    2012/061839 A2   5/2012
WO    2012/061839 A3   5/2012

OTHER PUBLICATIONS

Peterson et al.; "Fat Quantification Using Multiecho Sequences with Bipolar Gradients: Investigation of Accuracy and Noise Performance"; Magnetic Resonance in Medicine, vol. 71, No. 1, Feb. 14, 2013, pp. 219-229.

(Continued)

Primary Examiner — Nancy Bitar
(74) Attorney, Agent, or Firm — W&C IP

(57) ABSTRACT

It is proposed a method for post-processing images of an region of interest in a subject, the images being acquired with a magnetic resonance imaging technique, the method for post-processing comprising at least the step of: —unwrapping the phase of each image, —extracting a complex signal over echo time for at least one pixel of the unwrapped images, and —calculating fat characterization parameters by using a fitting technique applied on a model, the model being a function which associates to a plurality of parameters each extracted complex signal, the plurality of parameters comprising at least two fat characterization parameters, the magnitude error and the phase error generated by the use of the bipolar readout gradients, the fitting technique being a non-linear least-square fitting technique using pseudo-random initial conditions.

17 Claims, 6 Drawing Sheets

(51) Int. Cl.
  *G01R 33/561*  (2006.01)
  *G01R 33/565*  (2006.01)
  *A61B 5/00*  (2006.01)
(52) U.S. Cl.
  CPC ..... *G01R 33/5615* (2013.01); *G01R 33/5616* (2013.01); *G01R 33/5618* (2013.01); *G01R 33/56518* (2013.01); *G01R 33/56527* (2013.01); *G01R 33/56554* (2013.01)

(56) References Cited

U.S. PATENT DOCUMENTS

| | | | | |
|---|---|---|---|---|
| 2012/0268121 A1* | 10/2012 | Hernando | .......... | G01R 33/4828 |
| | | | | 324/309 |
| 2015/0061672 A1* | 3/2015 | Kannengiesser | ...... | A61B 5/055 |
| | | | | 324/309 |
| 2015/0309137 A1* | 10/2015 | Bydder | .............. | G01R 33/4828 |
| | | | | 324/309 |
| 2016/0041247 A1* | 2/2016 | Feiweier | ................ | A61B 5/055 |
| | | | | 324/309 |

OTHER PUBLICATIONS

Leporq et al.; "Quantification of the triglyceride fatty acid composition with 3.0 T MRI"; NMR in Biomedicine, vol. 27, No. 10, Aug. 14, 2014, pp. 1211-1221.
Peterson et al.; "Simultaneous Quantification of Fat Content and Fatty Acid Composition Using MR Imaging"; Magnetic Resonance in Medicine, vol. 69, No. 3, Mar. 1, 2013, pp. 688-697.
Zhong et al.; "Liver Fat Quantification Using a Multi-Step Adaptive Fitting Approach with Multi-Echo GRE Imaging"; Magnetic Resonance in Medicine, vol. 72, No. 5, Nov. 1, 2014, pp. 1353-1365.
Peterson et al.; "Relaxation Effects in MRI-Based Quantification of Fat Content and Fatty Acid Composition"; Magnetic Resonance in Medicine, vol. 72, No. 5, Dec. 10, 2013, pp. 1320-1329.
Berglund et al.; "Model-Based Mapping of Fat Unsaturation and Chain Length by Chemical Shift Imaging—Phantom Validation and In Vivo Feasibility"; Magnetic Resonance in Medicine, vol. 68, No. 6, Feb. 14, 2012, pp. 1815-1827.
Feng et al.; "Catalytic Multiecho Phase Unwrapping Scheme (CAMPUS) in Multiecho Gradient Echo Imaging: Removing Phase Wraps on a Voxel-by-Voxel Basis"; Magnetic Resonance in Medicine, vol. 70, No. 1, Jul. 1, 2013, pp. 117-126.
Lu et al.; "Water-Fat Separation with bipolar Multiecho Sequences"; Magnetic Resonance in Medicine, vol. 60, No. 1, Jun. 25, 2008, pp. 198-209.
Yu et al.; "Phase and Amplitude Correction for Multi-Echo Water-Fat Separation with Bipolar Acquisitions"; Journal of Magnetic Resonance Imaging, vol. 31, No. 5, Apr. 23, 2010, pp. 1264-1271.

* cited by examiner

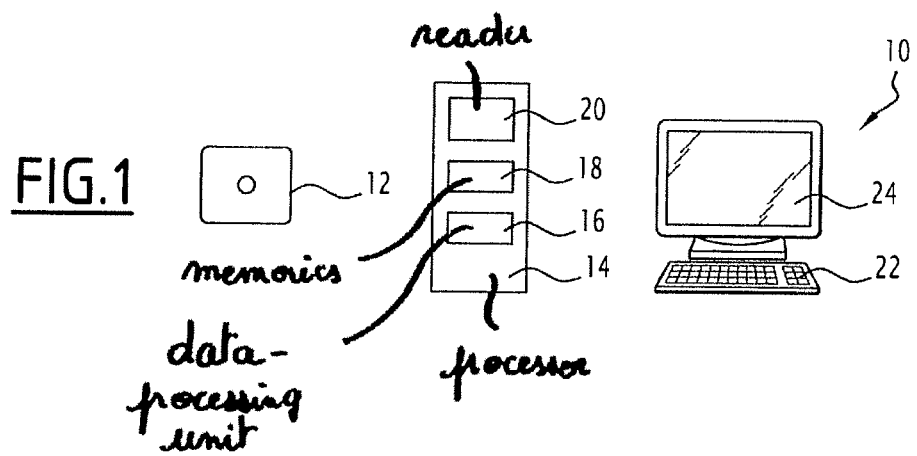
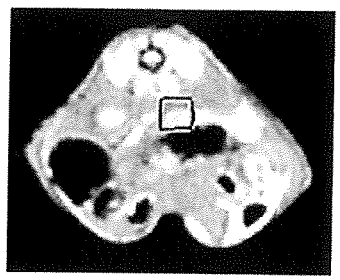
FIG.2
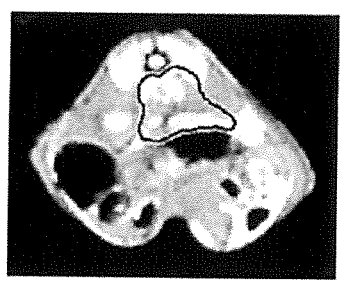
FIG.3
FIG.4
FIG.5
FIG.6
FIG.7

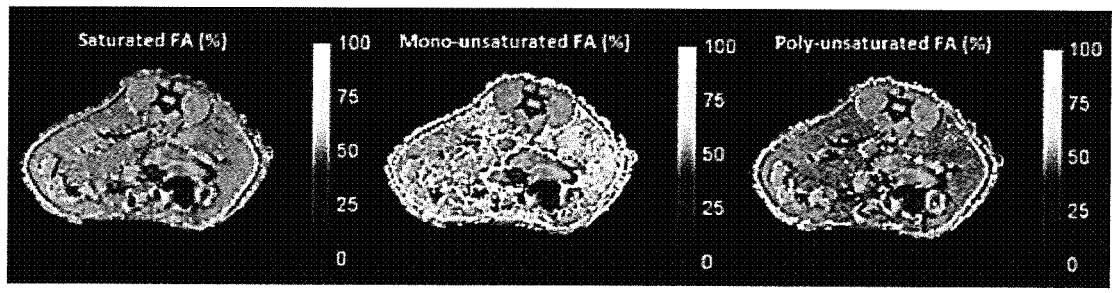
FIG.24  FIG.25  FIG.26
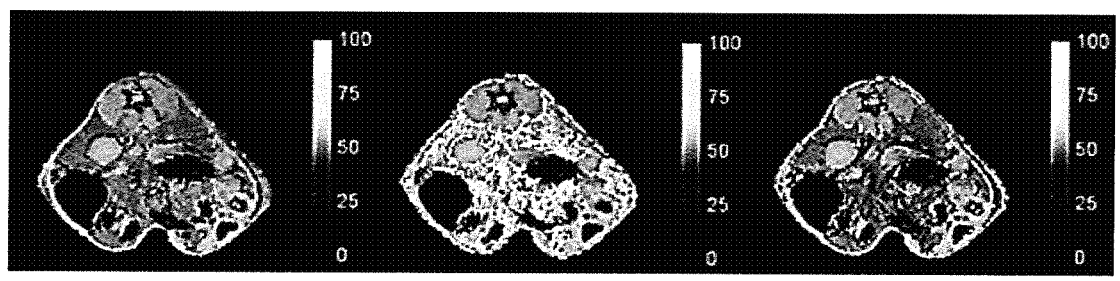
FIG.27  FIG.28  FIG.29
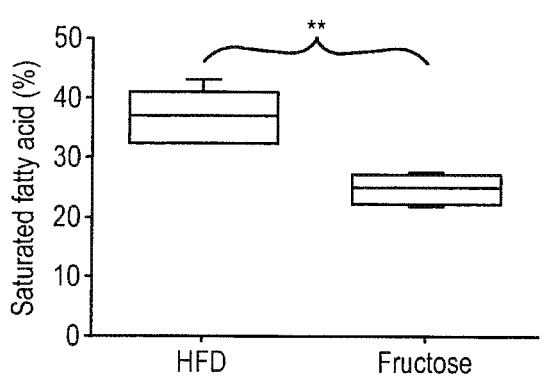 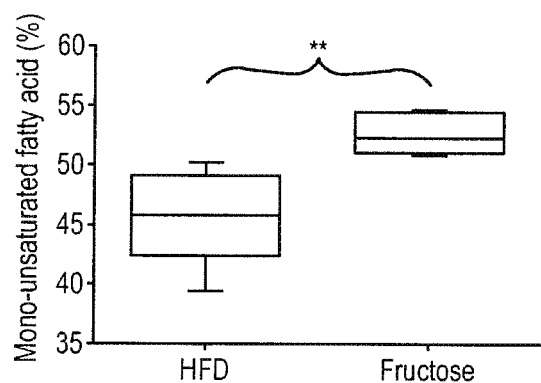
FIG.30  FIG.31

METHOD FOR FAT CHARACTERIZATION USING MRI IMAGES ACQUIRED USING A MULTIPLE GRADIENT-ECHO SEQUENCE WITH BIPOLAR GRADIENTS

TECHNICAL FIELD OF THE INVENTION

The invention relates to a method for post-processing images of a region of interest in a subject. The invention also concerns a method for predicting that a subject is at risk of suffering from an obesity related disease. The invention also relates to a method for diagnosing an obesity related disease. The invention also concerns a method for monitoring the responsiveness of a subject suffering from an obesity related disease to a treatment useful for said disease. The invention also relates to a method for screening a probiotic, a prebiotic, a chemical compound or a biological compound suitable for obtaining a treatment useful for an obesity related disease. The invention also concerns a method for monitoring the proportion of unsaturated fatty acids and proportion of saturated fatty acids in a region of interest in a subject. The invention also relates to a method for identifying a biomarker, the biomarker being a diagnostic biomarker of an obesity related disease, a susceptibility biomarker of an obesity related disease, a prognostic biomarker of an obesity related disease or a predictive biomarker in response to the treatment of an obesity related disease. The invention also relates to the associated device, computer program products and information supports.

BACKGROUND OF THE INVENTION

Suboptimal diet is the single leading modifiable cause of poor health in the world. High fat intake causes obesity and increases the risk of cardiovascular diseases, type-2 diabetes mellitus, and cancer. The metabolic risks are related to ectopic fat deposition in the abdomen and the liver and are influenced by the intake of saturated fatty acids (SFA).

Moreover, the protective effects of replacing SFA with polyunsaturated fatty acids (PUFA) have been demonstrated for coronary heart disease and for some cancers, especially when omega-3 PUFA are administered.

These points underscore the fact that obesity related diseases are caused not only by the total amount of fat, but also by visceral fat distribution and fatty acid composition.

Therefore, it is desirable to develop non-invasive methods to quantify the amount and composition of abdominal fat.

It is known from document WO 2012/061839 A2 techniques, apparatus and systems are described for using parameters including chain length, number of double bonds and number of double-double bonds of a complex, magnetic resonance imaging (MRI)-generated fat spectrum to determine the composition and properties of fat and to perform various diagnostic functions. In one aspect, a method using magnetic resonance imaging to characterize fat includes acquiring a magnetic resonance (MR) image that includes MR data from a target, determining fat characterization parameters based on the acquired MR data, and using the determined fat characterization parameters to produce a relationship between regions of fat and/or water in the MR image.

However, such technique is not usable in the context of high field preclinical magnetic resonance imaging systems.

SUMMARY OF THE INVENTION

The invention aims at providing a method which can be used in each case, and notably in the context of high field preclinical magnetic resonance imaging systems.

To this end, the invention concerns a method for post-processing images of a region of interest in a subject, the images being acquired with a magnetic resonance imaging technique, the magnetic resonance imaging technique involving successive echoes of a multiple-gradient echo sequence with bipolar readout gradients, each image associating to each pixel of the image the amplitude of the measured signal in the magnetic resonance imaging technique and the phase of the measured signal in the magnetic resonance imaging technique, the method for post-processing comprising at least the steps of unwrapping the phase of each image, to obtain unwrapped images, extracting a complex signal over echo time for at least one pixel of the unwrapped images, to obtain at least one extracted complex signal, and calculating fat characterization parameters by using a fitting technique applied on a model. The model is a function which associates to a plurality of parameters each extracted complex signal, the plurality of parameters comprising at least two fat characterization parameters, the magnitude error generated by the use of the bipolar readout gradients and the phase error generated by the use of the bipolar readout gradients and the fitting technique is a non-linear least-square fitting technique using pseudo-random initial conditions.

Thanks to the invention, images taken the context of high field preclinical magnetic resonance imaging systems may be post-processed to calculate fat characterization parameters with a good accuracy.

According to further aspects of the invention which are advantageous but not compulsory, the method for post-processing images might incorporate one or several of the following features, taken in any technically admissible combination:
 the fat characterization parameters are chosen in the group consisting of the number of double bounds, the number of methylene-interrupted double bounds and the chain length.
 the method for post-processing images further comprises the steps of determining the phase jump in the phase between two image, the first image being acquired at a first echo and the second image being acquired at a second consecutive echo, comparing the phase jump with a threshold value, and correcting the phase value when the phase jump is superior or equal to the threshold value.
 the model further depends on the complex intensity of water, the complex intensity of fat and a complex field map taking into account the effect of transversal relaxivity rate and the field inhomogeneity in the magnetic field used in the magnetic resonance imaging technique.
 the method for post-processing images further comprises the step of quantifying the proportion of unsaturated fatty acids and proportion of saturated fatty acids in the region of interest in the subject based on the calculated fat characterization parameters.
 the quantifying step comprises determining the proton density fat fraction and the fatty acid composition based on the calculated fat characterization parameters.

It is also proposed a method for predicting that a subject is at risk of suffering from an obesity related disease, the method for predicting at least comprising the step of carrying out the steps of the method for post-processing images of the subject as previously described, to obtain fat characterization parameters, and predicting that the subject is at risk of suffering from the obesity related disease based on the fat characterization parameters.

It also concerns a method for diagnosing an obesity related disease, the method for diagnosing at least comprising the step of carrying out the steps of the method for post-processing images of the subject as previously described, to obtain fat characterization parameters, and—diagnosing the obesity related disease based on the fat characterization parameters.

It is also proposed a method for monitoring the responsiveness of a subject suffering from an obesity related disease to a treatment useful for said disease, the method for monitoring the responsiveness comprising carrying out the steps of the method for post-processing images of the subject as previously described, to obtain fat characterization parameters before the treatment, carrying out the steps of the method for post-processing images of the subject as previously described, to obtain fat characterization parameters during or after the treatment, and comparing the fat characterization parameters before the treatment with the fat characterization parameters during or after the treatment, a difference between said fat characterization parameters being indicative that the treatment is effective.

It also concerns a method for screening a probiotic, a prebiotic, a chemical compound or a biological compound suitable for obtaining a treatment useful for an obesity related disease using the method for monitoring the responsiveness of a subject as previously described.

It is also proposed a method for monitoring the proportion of unsaturated fatty acids and proportion of saturated fatty acids in a region of interest in a subject, the method for monitoring at least comprising the step of imaging the region of interest in the subject by using an magnetic resonance imaging technique, the magnetic resonance imaging technique involving successive echoes of a multiple-gradient echo sequence with bipolar readout gradients, to obtain images, carrying out the steps of the method for post-processing the obtained images as previously described, to obtain fat characterization parameters, and quantifying the proportion of unsaturated fatty acids and proportion of saturated fatty acids in the region of interest in the subject based on the calculated fat characterization parameters.

According to a specific embodiment, the magnetic resonance imaging technique involves using a magnetic field value comprised between 1.0 T and 11.7 T.

It also relates to a method for identifying a biomarker, the biomarker being a diagnostic biomarker of an obesity related disease, a susceptibility biomarker of an obesity related disease, a prognostic biomarker of an obesity related disease or a predictive biomarker in response to the treatment of an obesity related disease, the method comprising the steps of carrying out the steps of the method for post-processing images as previously described, to obtain first fat characterization parameters from a subject suffering from the obesity related disease, carrying out the steps of the method for post-processing images as previously described, to obtain second fat characterization parameters from a subject not suffering from the obesity related disease, and selecting a biomarker based on the comparison of the first and second obtained parameters.

It also concerns a computer program product comprising instructions for carrying out the steps of a method for post-processing images as previously described when said computer program product is executed on a suitable computer device.

It is also proposed a computer program product comprising instructions for carrying out the steps of a method for predicting as previously described when said computer program product is executed on a suitable computer device.

It also concerns a computer program product comprising instructions for carrying out the steps of a method for diagnosing an obesity related disease as previously described when said computer program product is executed on a suitable computer device.

It is also proposed a computer program product comprising instructions for carrying out the steps of a method for identifying a biomarker as previously described when said computer program product is executed on a suitable computer device.

It is also proposed a device for monitoring the proportion of unsaturated fatty acids and proportion of saturated fatty acids in a region of interest in a subject, the device comprising a magnetic resonance imaging system adapted to image the region of interest in the subject by using a magnetic resonance imaging technique, the magnetic resonance imaging technique involving successive echoes of a multiple-gradient echo sequence with bipolar readout gradients, to obtain images and a controller. The controller is adapted to receive the obtained images of the region of interest from the magnetic resonance imaging system, each image associating to each pixel of the image the amplitude of the measured signal in the magnetic resonance imaging technique and the phase of the measured signal in the magnetic resonance imaging technique, unwrap the phase of each image, to obtain unwrapped images, extract a complex signal over echo time for at least one pixel of the unwrapped images and to obtain at least one extracted complex signal, calculate fat characterization parameters by using a fitting technique applied on a model. The model is a function which associates to a plurality of parameters each extracted complex signal, the plurality of parameters comprising at least two fat characterization parameters, the magnitude error generated by the use of the bipolar readout gradients and the phase error generated by the use of the bipolar readout gradients. The fitting technique is a non-linear least-square fitting technique using pseudo-random initial conditions. The controller is further adapted to quantify the proportion of unsaturated fatty acids and proportion of saturated fatty acids in the region of interest in the subject based on the calculated fat characterization parameters.

According to further aspects of the invention which are advantageous but not compulsory, the device for monitoring the proportion of unsaturated fatty acids and proportion of saturated fatty acids in an region of interest in a subject might incorporate one or several of the following features, taken in any technically admissible combination:
- the magnetic resonance imaging system is adapted to apply magnetic field whose magnetic field is comprised between 1.0 T and 11.7 T.
- the magnetic resonance imaging system is adapted to image a field of view defining a maximum perimeter, the subject having dimensions such that the subject be smaller than the region of interest delimited by the maximum perimeter.

BRIEF DESCRIPTION OF THE DRAWINGS

The invention will be better understood on the basis of the following description which is given in correspondence with the annexed figures and as an illustrative example, without restricting the object of the invention. In the annexed figures:

FIG. 1 shows schematically a system and a computer program product whose interaction enables to carry out a method for post-processing images;

FIGS. 2 to 7 illustrates the evolution of active contour on native magnitude images through segmentation algorithm iterations. A mask is built to select pixels without air and reduce computing time;

FIGS. 8 and 9 illustrate phase wraps which may disturb water-fat separation. In pixel close to field of view center (FIG. 8), unwrapped phase follows quasi-linear pattern suggesting that phase errors caused by bipolar gradients are not large. In peripheral pixel (FIG. 9), unwrapped phase follows non-linear pattern highlighting large phase errors in readout direction;

FIGS. 10 to 12 show consistent fat-water separation in each tube;

FIGS. 24 to 29 illustrate fatty acid (FA) composition maps (of visceral adipose tissue in two mice with different diets (high fat diet (FIGS. 24 to 26) and fructose diet (FIGS. 27 to 29));

FIGS. 30 to 32 illustrates fatty acid composition of visceral adipose tissue (fraction of saturated fatty acids, fraction of mono-saturated fatty acids and fraction of poly-unsaturated fatty acids) according to diet.

DETAILED DESCRIPTION OF SOME EMBODIMENTS

Figure 8:
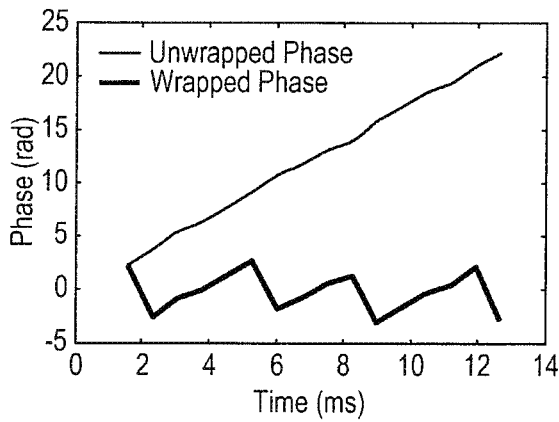
FIGS. 8 and 9 shows the wrapped and unwrapped phase evolution in pixel close to field of view center (FIG. 8) and in peripheral pixel (FIG. 9).

A system 10 and a computer program product 12 are represented in FIG. 1. The interaction between the computer program product 12 and the system 10 enables to carry out a method for post-processing images.

System 10 is a computer. In the present case, system 10 is a laptop.

More generally, system 10 is a computer or computing system, or similar electronic computing device adapted to manipulate and/or transform data represented as physical, such as electronic, quantities within the computing system's registers and/or memories into other data similarly represented as physical quantities within the computing system's memories, registers or other such information storage, transmission or display devices.

System 10 comprises a processor 14, a keyboard 22 and a display unit 24.

The processor 14 comprises a data-processing unit 16, memories 18 and a reader 20. The reader 20 is adapted to read a computer readable medium.

The computer program product 12 comprises a computer readable medium.

The computer readable medium is a medium that can be read by the reader of the processor. The computer readable medium is a medium suitable for storing electronic instructions, and capable of being coupled to a computer system bus.

Such computer readable storage medium is, for instance, a disk, a floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

A computer program is stored in the computer readable storage medium. The computer program comprises one or more stored sequence of program instructions.

The computer program is loadable into the data-processing unit and adapted to cause execution of the method for post-processing images when the computer program is run by the data-processing unit.

Operation of the system 10 is now described by illustrating an example of carrying out the method for post-processing images.

The images post-processed in the method for post-processing images are images of a region of interest in a subject.

The region of interest is adipose tissues or tissue containing fat.

The subject is usually a small animal, such as a rabbit or a mouse.

In the experience described in reference with FIGS. 2 to 32, the subjects are mice.

The images are acquired with a magnetic resonance imaging technique.

The magnetic resonance imaging technique involving successive echoes of a multiple-gradient echo sequence with bipolar readout gradients.

According to the specific embodiment described, the multiple-gradient echo sequence is a spoiled gradient echo sequence.

In addition, the magnetic resonance imaging technique is carried out by a preclinical system operating at magnetic field with a magnitude of 7.0 Tesla (T).

Each image associates to each pixel of the image the amplitude of the measured signal in the magnetic resonance imaging technique and the phase of the measured signal in the magnetic resonance imaging technique.

In other words, for each image, it can be defined a magnitude map and a phase map.

The method for post-processing images comprises four steps, which are a step of correcting, a step of extracting, a step of calculating and a step of quantifying.

At the step of correcting, a mask is built from the magnitude images to suppress background and air cavities to decrease overall computing time by reducing the number of processed pixels.

Segmentation is performed with an active contour approach which is based on techniques of curve evolution, Mumford-Shah function for segmentation and level sets. This method includes a model able to detect objects which boundaries are not necessarily defined by gradients (see notably FIGS. 2 to 7).

At the step of correcting, the phase of each image is unwrapped to obtain unwrapped images.

For this, the phase jump is determined in the phase between two images, the first image being acquired at a first echo and the second image being acquired at a second consecutive echo. The phase jump is compared with a threshold value, and the phase value is corrected when the phase jump is superior or equal to the threshold value.

Figure 9:
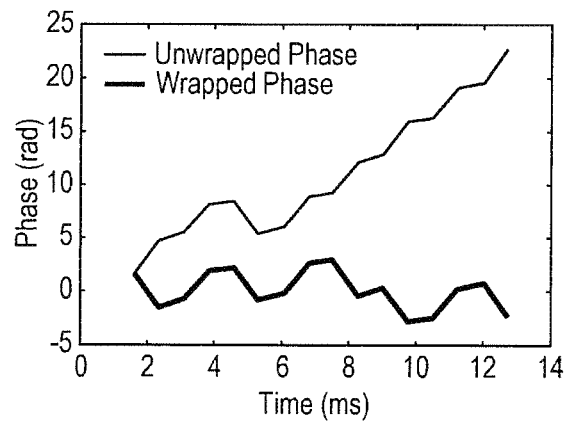

More precisely, a phase-time array was extracted pixel by pixel and individual points were corrected for wrap by adding multiples of $\pm 2\pi$ when absolute jumps between consecutive elements of the array were greater than or equal to a jump tolerance of $\pi$ radians (see FIGS. 8 and 9).

Then, corrected complex images are generated from the magnitude and the phase unwrapped images.

At the end of the correcting step, corrected complex images are obtained.

At the step of extracting, a complex signal over echo time for at least one pixel of the unwrapped images is extracted. According to the specific embodiment described, from multiple echo unwrapped complex images, a complex signal over echo time $S(t_n, x, y)$ is extracted pixel by pixel, $t_n$ being the time of the echo and x, y being spatial coordinates.

The complex signal over echo time corresponds to the complex gradient echo signal at time $t_n$.

At the end of the extracting step, for each pixel, the complex signal over echo time $S(t_n, x, y)$ is known.

Optionally, at the correcting step, phase images for zero (time independent) and first order (time-dependent) dephasings are also corrected.

Alternatively, the method for post-processing images comprises a step of providing corrected real images to be post-processed. At the step of calculating, fat characterization parameters are calculated by using a fitting technique applied on a model.

The model is a model for the complex gradient echo signal at time $t_n$ from a pixel containing water and fat with an unknown number of spectral components.

In other words, such model is a function which associates to a plurality of parameters each extracted complex signal.

The plurality of parameters comprises at least two fat characterization parameters, the magnitude error generated by the use of the bipolar readout gradients and the phase error generated by the use of the bipolar readout gradients.

Fat characterization parameters may be any parameters which enables to obtain information on the chemical structure of fat.

According to a specific embodiment, the fat characterization parameters are chosen in the group consisting of the number of double bounds ndb, the number of methylene-interrupted double bounds nmidb and the chain length CL.

The model is based on eight separate fat resonances.

For instance, the model is the following model:

$$\check{S}(t_{n,x,y}) = \left( \check{W} n_w + \check{F} \sum_{k=1}^{8} n_k(ndb, CL, nmidb) e^{2\pi i f_k t_n} \right) e^{2\pi i \check{\psi} t_n} e^{(-1)^n i \check{\theta}(x,y)}$$

where:
$\check{W}$ is the complex intensity of water,
$n_w$ is the number of protons in the water peak
$\check{F}$ is the complex intensity of fat,
$n_k(ndb, CL, nmidb)$ is the number of protons in the fat spectrum component k according to the number of double bounds ndb, the number of methylene-interrupted double bounds nmidb and the chain length CL,
$F_k$ is the frequency shift of the kth fat resonance with relation to water (considered on-resonance),
$\check{\psi}$ is a complex field map taking into account the effect of transversal relaxivity rate and the field inhomogeneity in the magnetic field used in the magnetic resonance imaging technique,
$\check{\theta}(x, y)$ being a complex error map depending from the magnitude error generated by the use of the bipolar readout gradients and the phase error generated by the use of the bipolar readout gradients It can be noticed that the model further depends on the complex intensity of water $\check{W}$, the complex intensity of fat $\check{F}$ and a complex field map $\check{\psi}$ taking into account the effect of transversal relaxivity rate and the field inhomogeneity in the magnetic field used in the magnetic resonance imaging technique.

$\check{\psi}$ is a complex field map summarizing the effect of both R2*(1/T2*) and $B_0$ field inhomogeneity according to:

$$\check{\psi} = \Delta + R^*_2$$

where R2* is the transversal relaxivity rate and $\Delta$ the $B_0$ field inhomogeneity.

To take into account the phase error and the amplitude modulation caused by the bipolar readout gradients, a complex error map $\check{\theta}(x, y)$ was included in the model. This latter induces a modulation in the signal according to the echo n polarity. This complex error map summarized both phase $\Phi$ and magnitude error $\varepsilon$ according to the following linear relationship:

$$\theta = \Phi - i\varepsilon$$

Therefore, in the example, the model depends from eleven parameters, which are the complex intensity of water $\check{W}$, the complex intensity of fat $\check{F}$, the number of double bounds ndb, the number of methylene-interrupted double bounds nmidb, the chain length CL, two parameters via the complex field map $\check{\psi}$, the magnitude error generated by the use of the bipolar readout gradients and the phase error generated by the use of the bipolar readout gradients via the complex error map $\check{\theta}$.

To obtain these eleven parameters, a fitting technique was used.

The fitting technique a non-linear least-square fitting technique using pseudo-random initial conditions.

As an example, the eleven parameters may be derived by using a non-linear least-square fit using the multi-start Levenberg-Marquardt algorithm.

In mathematics and computing, the Levenberg-Marquardt algorithm (LMA), also known as the damped least-squares method, is used to solve non-linear least squares problems. These minimization problems arise especially in least squares curve fitting.

The LMA interpolates between the Gauss-Newton algorithm (GNA) and the method of gradient descent. The LMA is more robust than the GNA, which means that in many cases it finds a solution even if it starts very far off the final minimum. For well-behaved functions and reasonable starting parameters, the LMA tends to be a bit slower than the GNA. LMA can also be viewed as Gauss-Newton using a trust region approach.

The LMA is a very popular curve-fitting algorithm used in many software applications for solving generic curve-fitting problems. However, as for many fitting algorithms, the LMA finds only a local minimum, which is not necessarily the global minimum.

A multi-start technique or the use of pseudo-random initial conditions corresponds to the use of a grid of pseudo-random initial conditions. This enables to improve the robustness of optimization and avoid multiple local minima problem.

In other words, the fitting technique is carried out a certain number of times, each time corresponding to different initial conditions.

For instance, the number of times is superior or equal to five, preferably superior or equal to ten, more preferably superior or equal to twenty.

According to a specific example, the number of times is equal to twenty.

Optionally, to decrease the degree of freedom, the chain length CL is expressed according to the number of double bounds ndb using a heuristic approximation. Such heuristic approximation is usually a linear relationship.

At the end of the calculating step, the fat characterization parameters are obtained.

At the step of quantifying, the proportion of unsaturated fatty acids and proportion of saturated fatty acids in the region of interest in the subject are obtained based on the calculated fat characterization parameters.

Preferably, at the step of quantifying, the proportions of saturated, monounsaturated and polyunsaturated fatty acids in the region of interest in the subject are quantified based on the calculated fat characterization parameters.

As an example, the quantifying step comprises determining the proton density fat fraction and the fatty acid composition based on the calculated fat characterization parameters.

According to a specific embodiment, the proton density fat fraction (PDFF) is calculated by using the following formula:

$$PDFF = \frac{\|\check{F}\|}{\|\check{W}\| + \|\check{F}\|}$$

For determining the fatty acid composition, it is proposed to use the following relations:

$$UFA = \frac{ndb - nmidb}{3}$$

and $$PUFA = \frac{nmidb}{3}$$

Where:
UFA is the unsaturated fatty acid fraction in %, and
PUFA is the polyunsaturated fatty acid fraction in %.

Optionally, determining the fatty acid composition may also comprise deducing the monounsaturated fatty acid fraction, which is generally labeled MUFA. For this, the following equation may be used:

MUFA=UFA−PUFA

Optionally, determining the fatty acid composition may also comprise calculating the saturated fatty acid fraction, which is generally labeled SFA. For this, the following equation may be used:

SFA=100−UFA

With bipolar acquisitions, the chemical shift, the errors resulting from eddy currents, field inhomogeneity and other system non-idealities appear in opposite directions at echoes with different gradient polarities. This induces phase errors which are modulated in opposite spatial directions for positive and negative gradient polarities, disrupting the inter-echo phase consistency that is critical for water-fat separation.

Moreover, due to the needed large read-out bandwidth, the frequency response of the receiver channel is not flat and causes an amplitude variation in the read-out direction, which leads to a discrepancy in each other echo.

Including a complex error map in the model to correct for the phase errors and the amplitude modulation caused by the bipolar acquisition reveals to be an efficient means to cope with these problems This results in images which can be acquired with short echo spacing using bipolar readout gradients, to obtain adequate spatial resolution in small animals.

Therefore, this method is the first to propose a magnetic resonance imaging method able to quantify the triglyceride fatty acid composition in small animals at 7.0 T.

In addition, with the proposed method for post-processing images, the chemical ambiguities arising from the inability to know, due to phase wrapping, whether the phase difference is between water and fat, or vice versa is corrected. This avoids an ambiguity on the parametric maps that can lead to a local swap of fat and water, where the fat estimate appears in the water only map, and vice versa.

For this, it is proposed to directly correct the native phase images for wrap before the complex signal reconstruction by making the assumption that a phase jump greater than π between two consecutive echoes corresponds to a phase wrap. The use of the spatial rather than the temporal information is also possible to unwrap the phase images. These spatial approaches include those relying on region merging based on a cost function or those using gradient matching based on the assumption that a wrapped phase image should have the same gradient than the original image except at the points where wraps occur. The advantage of the temporal information method proposed is the reduction in time calculation and the independence from the initialization.

Such method for post-processing images may notably be used in a method for predicting that the subject is at risk of suffering from an obesity related disease.

An obesity related disease is a cancer, type 2 diabetes, a heart disease, a liver disease or a non-alcoholic fatty liver diseases (NAFLD). Nonalcoholic fatty liver disease (NAFLD) and its most severe form, nonalcoholic steatohepatitis (NASH), are associated with high fat diet, high triglyceride levels, obesity, the metabolic syndrome and type II diabetes, and pose an increased risk of cardio vascular disease. NAFLD is an accumulation of fat in the liver that is not a result of excessive consumption of alcohol. 15% to 25% of cases of NAFLD progress and are associated with inflammation and liver damage; this condition is referred to as NASH. NASH is associated with an increased risk of developing liver cirrhosis and subsequence complications, including hepatocellular carcinoma.

The method for predicting comprises a step of carrying out the steps of the method for post-processing images of the subject as previously described, to obtain fat characterization parameters.

The method for predicting also comprises a step of predicting that the subject is at risk of suffering from the obesity related disease based on the fat characterization parameters.

Such method for post-processing images may also be used in a method for diagnosing an obesity related disease.

The method for diagnosing comprises a step of carrying out the steps of the method for post-processing images of the subject as previously described, to obtain fat characterization parameters.

The method for diagnosing also comprises a step of diagnosing the obesity related disease based on the fat characterization parameters.

Such method for post-processing images may also be used in a method for monitoring the responsiveness of a subject suffering from an obesity related disease to a treatment useful for said disease. The method for monitoring the responsiveness comprising a step of carrying out the steps of the method for post-processing images of the subject as previously described, to obtain fat characterization parameters before the treatment, a step of carrying out the steps of the method for post-processing images of the subject as previously described, to obtain fat characterization parameters during or after the treatment, and a step of comparing the fat characterization parameters before the treatment with the fat characterization parameters during or after the treatment, a difference between said fat characterization parameters being indicative that the treatment is effective.

Such method for post-processing images may also be used in a method for screening a probiotic, a prebiotic, a chemical compound or a biological compound suitable for obtaining a treatment useful for an obesity related disease using the method for monitoring the responsiveness of a subject as previously described.

Such method for post-processing images may also be used in a method for monitoring the proportion of unsaturated fatty acids and proportion of saturated fatty acids in the region of interest in the subject.

The method for monitoring comprises three steps: imaging, carrying out and quantifying.

At the step of imaging, the region of interest in the subject is imaged by using a magnetic resonance imaging technique, the magnetic resonance imaging technique involving successive echoes of a multiple-gradient echo sequence with bipolar readout gradients, to obtain images.

According to a specific embodiment, the magnetic resonance imaging technique involves using a magnetic field value comprised between 1.0 T and 11.7 T.

At the step of carrying out, the steps of the method for post-processing images of the subject as previously described are carried out to obtain fat characterization parameters.

At the step of quantifying, the proportion of unsaturated fatty acids and the proportion of saturated fatty acids in the region of interest in the subject are quantified based on the calculated fat characterization parameters.

Preferably, at the step of quantifying, the proportion of saturated, monounsaturated and polyunsaturated fatty acids in the region of interest in the subject are quantified based on the calculated fat characterization parameters.

Such method for monitoring is a non-invasive which can be carried out in vivo, ex vivo and in vitro.

Such method for post-processing images may also be used for a method for identifying a biomarker, the biomarker being a diagnostic biomarker of an obesity related disease, a susceptibility biomarker of an obesity related disease, a prognostic biomarker of an obesity related disease or a predictive biomarker in response to the treatment of an obesity related disease. The method for identifying a biomarker comprises the steps of carrying out the steps of the method for post-processing images, to obtain first fat characterization parameters from a subject suffering from the obesity related disease, carrying out the steps of the method for post-processing images, to obtain second fat characterization parameters from a subject not suffering from the obesity related disease and selecting a biomarker based on the comparison of the first and second obtained parameters.

Such method may be implemented on a device for monitoring the proportion of unsaturated fatty acids and proportion of saturated fatty acids in the region of interest in the subject.

Figure 33:
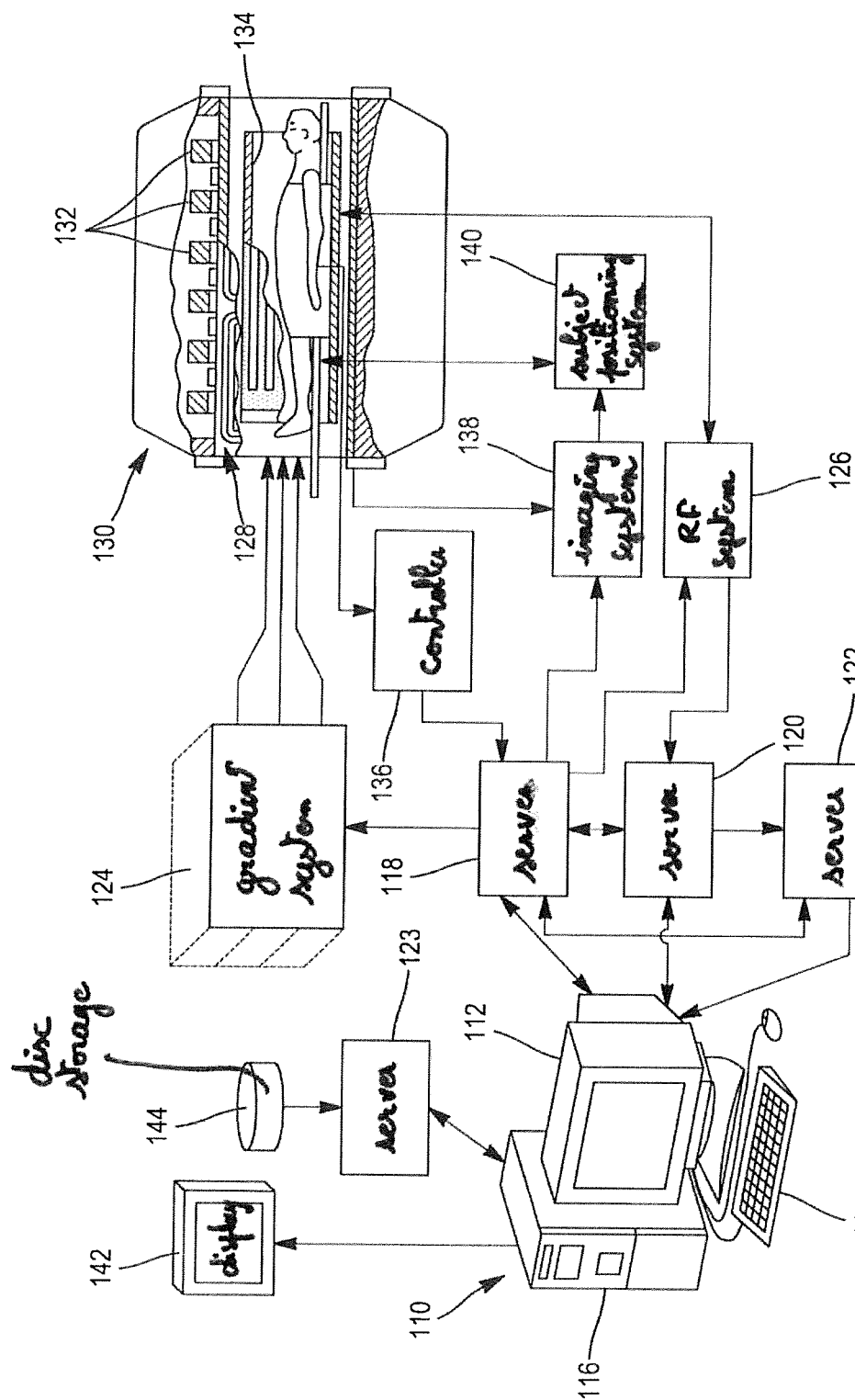
FIG. 33 is a schematic representation of a device for monitoring the proportion of unsaturated fatty acids and proportion of saturated fatty acids in a region of interest in a subject.

An example of such device is illustrated on FIG. 33.

The device comprises a controller 110, four servers and a magnetic resonance imaging system 138. The four servers are a pulse sequence server 118, a data acquisition server 120, a data processing server 122 and a data store server 123.

The controller 110 is adapted to receive the obtained images of the region of interest from the magnetic resonance imaging system 138, each image associating to each pixel of the image the amplitude of the measured signal in the magnetic resonance imaging technique and the phase of the measured signal in the magnetic resonance imaging technique, The controller 110 is also adapted to unwrap the phase of each image, to obtain unwrapped images.

The controller 110 is further adapted to extract a complex signal over echo time for at least one pixel of the unwrapped images, to obtain at least one extracted complex signal, The controller 110 is also adapted to calculate fat characterization parameters by using the fitting technique previously described.

The controller 110 is also adapted to quantify the proportion of unsaturated fatty acids and proportion of saturated fatty acids in the region of interest in the subject based on the calculated fat characterization parameters.

The controller 110 provides the operator interface which enables scan prescriptions to be entered into the magnetic resonance imaging system 138.

According to the embodiment of FIG. 33, the controller 110 is a workstation.

The controller 110 comprises a display 112, a keyboard 114, a processor 116.

The processor 116 is a commercially available programmable machine running a commercially available operating system.

The controller 110 is coupled to the four servers 118, 120, 122 and 123.

According to the example of FIG. 33, the data store server 123 is performed by the processor 116 and associated disc drive interface circuitry.

The remaining three servers 118, 120 and 122 are performed by separate processors mounted in a single enclosure and interconnected using a 64-bit backplane bus. The pulse sequence server 118 employs a commercially available microprocessor and a commercially available quad communication controller. The data acquisition server 120 and data processing server 122 both employ the same commercially available microprocessor and the data processing server 122 further includes one or more array processors based on commercially available parallel vector processors.

The controller 110 and each processor for the servers 118, 120 and 122 are connected to a serial communications network. This serial network conveys data that is downloaded to the servers 118, 120 and 122 from the controller 110. The network conveys tag data that is communicated between the servers 118, 120, 122 and 123 and between the controller 110. In addition, a high speed data link is provided between the data processing server 122 and the workstation 10 in order to convey image data to the data store server 123.

The pulse sequence server 118 functions in response to program elements downloaded from the controller 110 to operate a gradient system 124 and an RF system 126. Gradient waveforms necessary to perform the prescribed scan are produced and applied to the gradient system 124 which excites gradient coils in an assembly 128 to produce the magnetic field gradients $G_x$, $G_y$, and $G_z$ used for position encoding nuclear magnetic resonance NMR signals. NMR is a physical property according to which the nuclei of atoms absorb and re-emit electromagnetic energy at a specific resonance frequency in the presence of a magnetic field.

The gradient coil assembly 128 forms part of a magnet assembly 130 which includes a polarizing magnet 132 and a whole-body RF coil 134.

RF excitation waveforms are applied to the RF coil 134 by the RF system 126 to perform the prescribed magnetic resonance pulse sequence. Responsive NMR signals detected by the RF coil 134 are received by the RF system 126, amplified, demodulated, filtered and digitized under direction of commands produced by the pulse sequence server 118. The RF system 126 includes an RF transmitter for producing a wide variety of RF pulses used in MR pulse sequences. The RF transmitter is responsive to the scan prescription and direction from the pulse sequence server 118 to produce RF pulses of the desired frequency, phase and pulse amplitude waveform. The generated RF pulses may be applied to the whole body RF coil 134 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal.

The magnitude of the received NMR signal may thus be determined at any sampled point by the square root of the sum of the squares of the I and Q components:

$$M = \sqrt{I^2 + Q^2}$$

and the phase of the received NMR signal may also be determined by the following equation:

$$\Phi = \tan^{-1}\left(\frac{Q}{I}\right)$$

The pulse sequence server 118 also optionally receives patient data from a physiological acquisition controller 136. The controller 136 receives signals from a number of different sensors connected to the subject, such as ECG signals from electrodes or respiratory signals from a bellows. Such signals are typically used by the pulse sequence server 118 to synchronize, or "gate", the performance of the scan with the subject's respiration or heart beat.

The pulse sequence server 118 also connects to a scan room interface circuit 138 which receives signals from various sensors associated with the condition of the subject and the magnet system. It is also through the scan room interface circuit 138 that a subject positioning system 140 receives commands to move the subject to desired positions during the scan.

It should be apparent that the pulse sequence server 118 performs real-time control of magnetic resonance imaging system elements during a scan. As a result, the hardware elements of the pulse sequence server 118 are operated with program instructions that are executed in a timely manner by run-time programs. The description components for a scan prescription are downloaded from the controller 110 in the form of objects. The pulse sequence server 118 contains programs which receive these objects and converts them to objects that are employed by the run-time programs.

The digitized NMR signal samples produced by the RF system 126 are received by the data acquisition server 120. The data acquisition server 120 operates in response to description components downloaded from the controller 110 to receive the real-time NMR data and provide buffer storage such that no data is lost by data overrun. In some scans the data acquisition server 120 does little more than pass the acquired NMR data to the data processor server 122. However, in scans which require information derived from acquired NMR data to control the further performance of the scan, the data acquisition server 120 is programmed to produce such information and convey it to the pulse sequence server 118. For example, during prescans NMR data is acquired and used to calibrate the pulse sequence performed by the pulse sequence server 118. Also, navigator signals may be acquired during a scan and used to adjust RF or gradient system operating parameters or to control the view order in which k-space is sampled. And, the data acquisition server 120 may be employed to process NMR signals used to detect the arrival of contrast agent in an MRA scan. In all these examples the data acquisition server 120 acquires NMR data and processes it in real-time to produce information which is used to control the scan.

The data processing server 122 receives NMR data from the data acquisition server 120 and processes it in accordance with description components downloaded from the controller 110. Such processing may include Fourier transformation of raw k-space NMR data to produce two or three-dimensional images.

Images reconstructed by the data processing server 122 are conveyed back to the controller 110 where they are stored. Real-time images are stored in a data base memory cache (not shown) from which they may be output to operator display 112 or a display 142 which is located near the magnet assembly 130 for use by attending physicians. Batch mode images or selected real time images are stored in a host database on disc storage 144. When such images have been reconstructed and transferred to storage, the data processing server 122 notifies the data store server 123 on the controller 10.

The magnetic resonance imaging system 138 is adapted to image the region of interest in the subject by using a magnetic resonance imaging technique, the magnetic resonance imaging technique involving successive echoes of a multiple-gradient echo sequence with bipolar readout gradients, to obtain images.

The magnetic resonance imaging system 138 is further adapted to apply a magnetic field whose magnetic field value comprised between 1.0 T and 11.7 T.

The magnetic resonance imaging system 138 is adapted to image a field of view defining a maximum perimeter.

In a specific embodiment, the subject has dimensions such that the subject be smaller than the region of interest delimited by the maximum perimeter.

As a consequence, the subject is a small animal, as a rabbit or a mouse.

Experimental Section

MR Acquisition

The magnetic resonance imaging data were collected on a Bruker Pharmascan 7.0 T system (Bruker, Ettlingen, Germany) equipped with a shielded gradient set (300 mT·m$^{-1}$ maximum gradient amplitude and 80 mm inner diameter) and a $^1$H transmit-receive quadrature coil with 40 mm inner diameter.

First, an anatomic acquisition was performed with a T$_2$-weighted 2D RARE sequence with the following parameters:
- chemical fat saturation;
- TE: 11 ms;
- field of view: 40×40 mm$^2$;
- acquisition matrix: 256$^2$;
- 30 axial slices;
- slice thickness: 1 mm; RARE factor: 8, and
- 2 signal averages.

The acquisition was synchronized with respiration using balanced acquisitions over several respiratory periods with an effective TR of about 4.5 s.

For fat-water separation, a 2D multiple spoiled gradient echo sequence with bipolar readout gradients was used. Sixteen echoes were acquired (first echo: 1.58 ms and echo spacing: 0.74 ms). The acquisition parameters were:
- spoiler gradient duration: 1.5 ms and 0.8 ms according to readout and phase respectively;
- TR: 900 ms;
- hermitian pulse: 20°,
- receiver bandwidth: 300 KHz, and
- 8 signal averages.

In addition, geometric parameters were:
- field of view: 45 mm$^2$, acquisition matrix: 128$^2$,
- 20 transverse slices of 1 mm thick.

Phase and magnitudes images were saved systematically. The acquisition was synchronized with the respiration in animals. Prescription of localization was performed using anatomic images provided with the T$_{2w}$ RARE acquisition.

Post-Processing Algorithm

The post-processing algorithm was developed with Matlab r2012a (The MathWorks, Natick, Mass.).

The post-processing algorithm corresponds to the method for post-processing images as previously described.

Phantom Studies

To evaluate the accuracy of PDFF quantification, a phantom of fat-water emulsions with fat fractions between 0 and 60% was made.

Hazelnut oil was used as dispersed phase. The aqueous phase was prepared by dispersing the surfactant (Brij S100: polyoxyethylene 100 stearyl ether, Sigma-Aldrich, Saint-Louis, Mo., USA) in ultrapure water under continuous agitation for four hours using a magnetic stirrer.

The nominal weight fraction ($W_{emulsion}$) of the oil is defined as:

$$W_{emulsion} = \frac{m_{oil}}{(m_{oil} + m_{aqueous})}$$

where:

$m_{oil}$ is the weight of the oil phase, and $m_{aqueous}$ is the weight of the aqueous phase.

In addition, the surfactant weight fraction $W_{surfactant}$ was fixed at 4%.

The surfactant weight fraction $W_{surfactant}$ is given by the following formula:

$$W_{surfactant} = \frac{m_{surfactant}}{m_{oil}}$$

where:

$m_{surfactant}$ is the weight of surfactant.

Emulsions were prepared by dropwise addition of oil into the aqueous phase under continuous stirring for five minutes using an Ultra-Turrax (IKA T18 Basic, IKA-Labortechnik, Staufen, Germany) homogenizer operated at 25000 rpm.

The emulsions were sonicated using a stick sonicator (U200S control IKA-Labortechnik, Staufen, Germany) allowing amplitude and cycle variations.

To obtain a particle size distribution similar to that of fat vesicles in liver steatosis, the emulsions were stirred for 15 minutes with 50% cycle and 100% amplitude.

The mean diameters of the emulsion droplets were measured with laser light scattering (Zeta sizer Nano ZS Malvern Instrument, Worcestershire, United Kingdom).

All emulsions were stored in closed vials at room temperature.

To evaluate the accuracy of fatty acid quantification, a phantom with different fatty acid compositions was obtained by filling seven vials with different vegetable oils: olive, sunflower, walnuts, peanuts, hazelnuts, grape seed and canola.

The chemical constitution of each oil (i.e. proportion of each fatty acid) was obtained from known data.

Theoretical number of double bounds ndb was calculated according to the following formula:

$$ndb = \left(\frac{1}{M}\sum_n^1 n \times m_{UFAn}\right) \times 3$$

where:

$m_{UFAn}$ is the mass of an UFA group with n double bonds and M is the total mass.

Theoretical number of methylene interrupted double bounds nmidb was calculated according to:

$$nmidb = \left(\frac{m_{PUFA}}{M}\right) \times 3$$

where:

$m_{PUFA}$ is the mass of an PUFA group with n double bonds and M is the total mass.

The phantoms were scanned with the MR protocol described above.

Animal Studies

Magnetic resonance imaging was performed in 11 female athymic nude mice (Harlan Laboratories, Gannat, France) receiving two different diets during 14 weeks before magnetic resonance imaging.

Seven received a high fat diet (Altromin Spezialfutter GmbH, Bielefeld, Germany) which is mainly composed of SFA (composition; SFA: 176.9 g·Kg$^{-1}$, MUFA: 121 g·Kg$^{-1}$ and PUFA: 32.6 g·Kg$^{-1}$).

Four received a fructose diet (Altromin Spezialfutter GmbH, Bielefeld, Germany) containing lipids mainly composed of PUFA (composition; SFA: 8.9 g·Kg$^{-1}$, MUFA: 22.4 g·Kg$^{-1}$ and PUFA: 70.9 g·Kg$^{-1}$).

The detailed fatty acid composition of each diet is summarized in the following Table 1.

TABLE 1

Fatty acid composition of the high fat and fructose diets.

| Fatty acids | High fat diet | Fructose diet |
|---|---|---|
| Saturated fatty acid | | |
| C-4:0 | 4.43 | 0 |
| C-7:0 | 2.53 | 0 |
| C-8:0 | 0.63 | 0 |
| C-10:0 | 3.12 | 0.005 |
| C-12:0 | 3.37 | 0.005 |
| C-14:0 | 17.0 | 0.005 |
| C-15:0 | 1.27 | 0.005 |
| C-16:0 | 92.5 | 5.4 |
| C-18:0 | 48.5 | 2.5 |
| C-20:0 | 3.53 | 0.5 |
| C-22:0 | 0 | 0.5 |
| Total (g · Kg$^{-1}$)/Proportion (%) | 176.9/53.5 | 8.9/8.7 |
| Mono-unsaturated fatty acids | | |
| C-16:1 | 9.6 | 0.005 |
| C-18:1 | 109 | 21.9 |
| C-20:1 | 2.47 | 0.5 |
| C-22:1 | 0.17 | 0.005 |
| C-24:1 | 0 | 0.005 |
| Total (g · Kg$^{-1}$)/proportion (%) | 121/36.6 | 22.4/21.9 |
| Poly-unsaturated fatty acids | | |
| C-18:2 | 29.3 | 70.1 |
| C-20:2 | 1.03 | 0.5 |
| C-18:3 | 1.85 | 0.3 |
| C-20:4 | 0.41 | 0.005 |
| C-20:5 | 0 | 0.005 |
| C-22:6 | 0 | 0.005 |
| Total (g · Kg$^{-1}$)/proportion (%) | 32.6/9.90 | 70.9/69.4 |

The diets cause fat accumulation mainly in visceral adipose tissues and liver.

The animals were housed in the animal facility of University Paris Diderot (Animalerie site Xavier Bichat, agreement number: B75-18-01), under controlled temperature, with a 12 h light-dark cycle.

The experiments were conducted according to the procedures approved by the Institutional Animal Care and Ethical Committee of our institution.

The mice were imaged with the same acquisition protocol used for the phantom experiments.

Animals were anesthetized by inhalation of 2% isoflurane.

The body temperature was maintained inside the magnet at 37° C. by warm water circulation. A pressure sensor was used to monitor the respiratory cycle.

Statistical Analysis

All results measured on the parametric maps are expressed as mean±standard deviation.

For the phantom study, the comparison between theoretical and experimental data was performed using linear regression.

For the in vivo study, differences of fatty acid composition according to diet were investigated with the non-parametric Mann-Whitney test.

A significant difference was accepted for a p-value smaller than 0.05.

Results of the Phantom Studies

The mean diameter of the emulsion droplets ranged between 360 and 480 nm.

The emulsions did not show any phase separation during the course of the study

Figures 10, 11, 12:
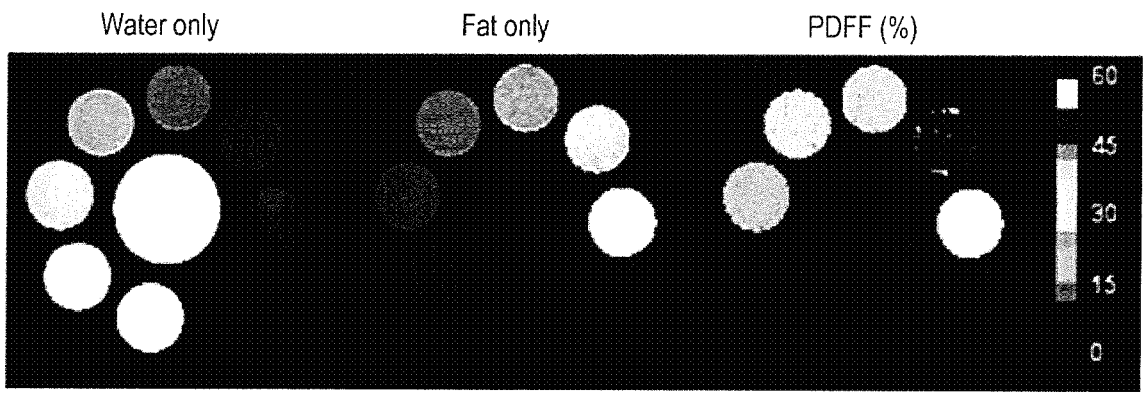
FIGS. 10 to 12 illustrate water and fat images, and proton density fat fraction (PDFF) maps of fat-water emulsions with different fat fractions (0, 10, 20, 30, 40, 50 and 60%, starting left bottom).

Proton density fat fractions were 1.1±0.5; 9.0±0.9; 18.3±0.9; 28.0±1.0; 38.7±1.2; 49.1±1.6 and 58.8±1.9% for the emulsions containing 0, 10, 20, 20, 40, 50 and 60% fat respectively (see notably FIGS. 10 to 12).

The theoretical number of double bounds ndb value and the theoretical number of methylene-interrupted double bounds nmidb values obtained from mass composition of each oil, and the number of double bounds ndb and the number of methylene-interrupted double bounds nmidb measurements calculated from the Magnetic resonance imaging data are shown in Table 2.

TABLE 2

Theoretical and measured number of double bounds (ndb), number of methylene interrupted double bonds (nmidb) and T2* of each oil.

| | ndb | | nmidb | | |
|---|---|---|---|---|---|
| Oil | Theoretical | Measured | Theoretical | Measured | T2* (ms) |
| Peanut | 3.39 | 3.68 ± 0.14 | 1.01 | 0.70 ± 0.15 | 33.7 ± 2.0 |
| Canola | 3.98 | 3.79 ± 0.15 | 1.05 | 1.03 ± 0.16 | 30.7 ± 1.6 |
| Sunflower | 4.59 | 4.49 ± 0.13 | 1.95 | 1.67 ± 0.15 | 30.4 ± 1.7 |
| Olive | 2.86 | 2.78 ± 0.14 | 0.32 | 0.22 ± 0.09 | 37.5 ± 1.7 |
| Walnut | 5.40 | 5.39 ± 0.10 | 2.32 | 2.37 ± 0.20 | 30.1 ± 1.6 |
| Hazelnut | 3.05 | 2.91 ± 0.14 | 0.27 | 0.33 ± 0.14 | 34.5 ± 2.7 |
| Grape seed | 4.98 | 4.91 ± 0.13 | 2.18 | 1.94 ± 0.15 | 29.0 ± 1.3 |

Figure 13:
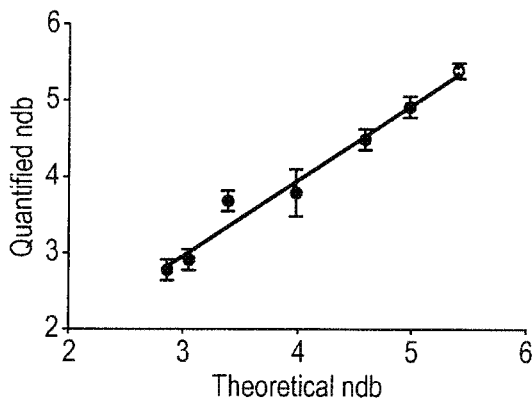
FIG. 13 shows the linear regression between theoretical and measured values for the number of double bounds ndb (y=0.99 x+0.012)

As shown on FIG. 13, the linear regressions between the theoretical and measured values were y=0.95 x−0.06, (95% confidence bounds: y=0.75 x−0.37/y=1.15 x+0.25), $R^2$=0.99, p<0.0001 for the ndb value.

Figure 14:
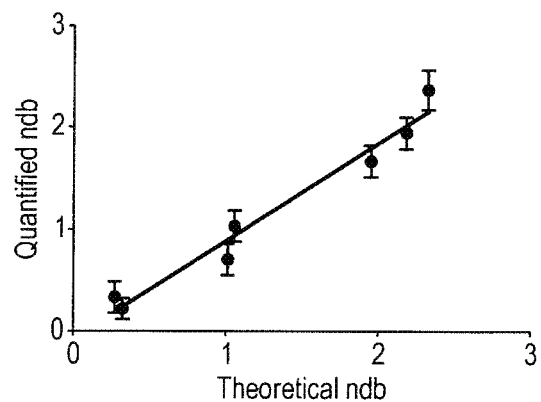
FIG. 14 shows the linear regression between theoretical and measured values for the number of methylene-interrupted double bounds nmidb (y=0.95 x−0.06)

As shown on FIG. 14, the linear regressions between the theoretical and measured values were y=0.99 x+0.012, (95% confidence bounds: y=0.80 x−0.74/y=1.16 x+0.77), $R^2$=0.99, p<0.0001 for the nmid value.

Figure 15:
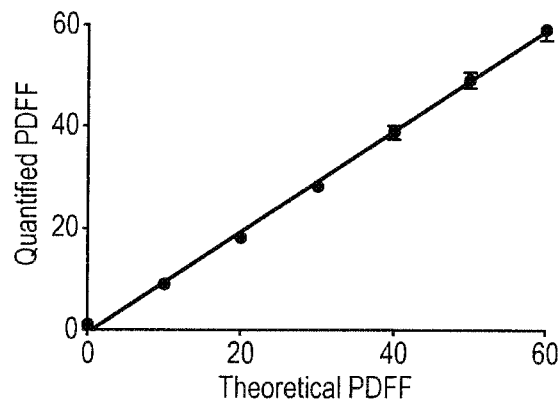
FIG. 15 shows the linear regression between theoretical and measured values for PDFF (y=0.98 x−0.33)
Figures 16, 17, 18, 19:
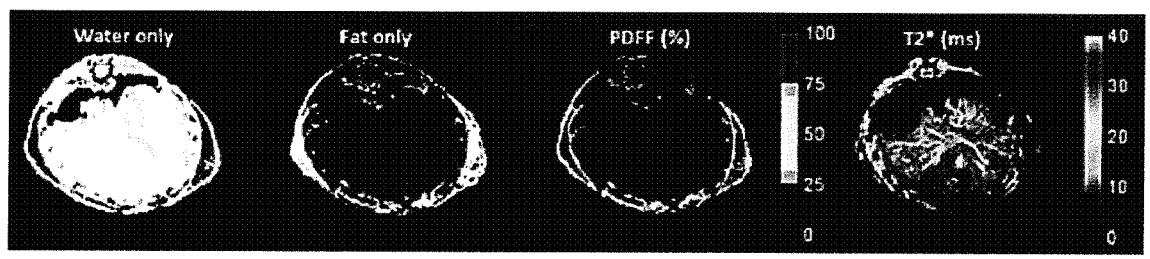
FIGS. 16 to 23 represent water and fat images and parametric maps (PDFF and T2*) computed with the proposed method. Images are acquired on high fat diet mouse and presented at two different slice levels. Mean PDFF and T2* in liver are 9.1% and 8.0 ms respectively.
Figures 20, 21, 22, 23:
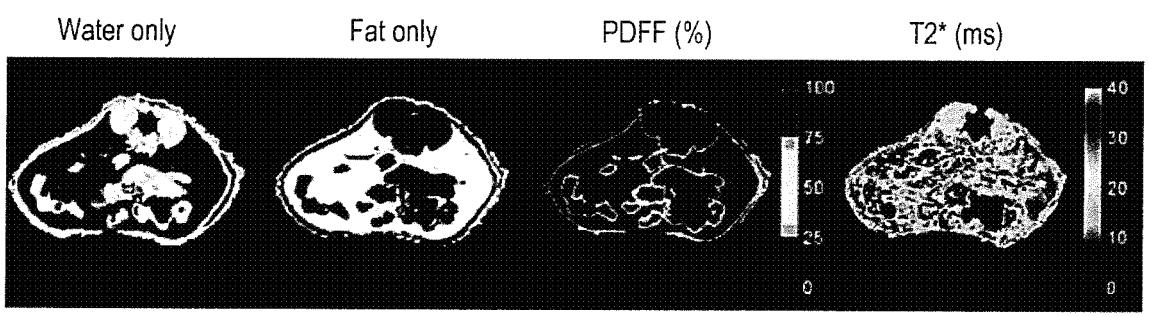

As shown on FIG. 15, the linear regressions between the theoretical and measured values were y=0.98 x−0.33, (95% confidence bounds: y=0.93 x−2.0/y=1.02 x+1.36), $R^2$=0.99, p<0.0001 for the PDFF value.

Each figure corresponds to a good agreement between theoretical and measured values.

Animal Studies

An illustration of fat and water only images, PDFF and T2* map is provided in FIGS. 16 to 23. Liver PDFF was smaller in the fructose group (7.7%±1.5%) than in high fat group (8.4%±1.2%). Mean liver T2* were 10.7 ms±1.5 and 8.4±1.2 ms for the fructose and high fat groups respectively.

Figure 32:
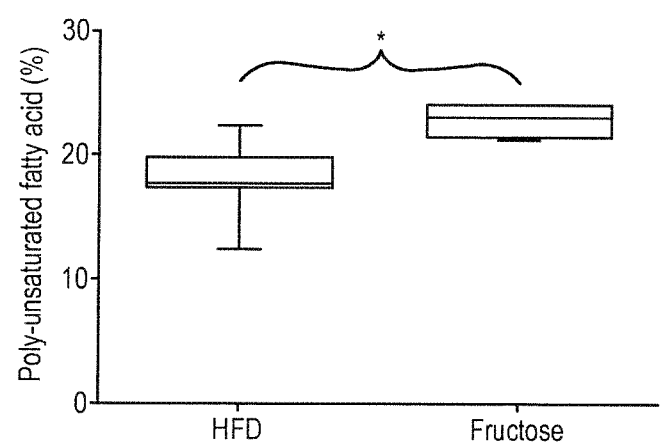

Others results related to the animal studies are illustrated by FIGS. 24 to 29 on the one hand and by FIGS. 30 to 32 on the other hand.

Maps of FIGS. 24 to 29 illustrate differences in visceral fatty acid composition according to diet: fractions of polyunsaturated and monounsaturated fatty acids are higher in fructose diet than in high fat diet, whereas fraction of saturated fatty acids are higher in high fat diet.

When contemplating FIGS. 30 to 32, it appears that, in high fat diet (HFD), visceral adipose tissue is significantly more saturated than in fructose diet (p<0.01). Both mono- and poly-unsaturated fatty acids are lower in high fat diet (p<0.01 and 0.05 respectively) than in fructose diet.

Thus, regarding the fatty acid composition in the visceral adipose tissue, both ndb and nmidb were smaller in the high fat group (2.44±0.19 and 0.54±0.09) than in the fructose group (2.94±0.12 and 0.69±0.04). Therefore, SFA was significantly higher in the high fat group than in the fructose group (36.7±4.4 versus 24.8±2.9, p<0.01), whereas MUFA and PUFA were significantly lower in high fat group than in fructose group (45.4±3.7 versus 52.4±1.8, p<0.01 and 17.9±3.0 versus 22.8±1.2, p<0.05 respectively).

CONCLUSION

Suboptimal diets, especially diets rich in SFA and poor in omega-3 PUFA, are a leading cause of obesity and its related morbidity. Classically, dietary assessment is based on reports of food intake. These reports have, however, several limitations that may weaken both the accuracy and precision of the measurements, such as under-reporting of respondents, interviewer bias and lack of well-matched food composition databases. Fatty acid biomarkers in blood or tissues are more accurate and convenient for estimating the long-term dietary fatty acid intake. Adipose tissue fatty acid composition is considered a gold standard for the representation of long-term (>1 year) dietary fatty acid intake because of its slow turnover time. However, fatty acid composition in the metabolically active deposition sites such as the mesentery, omentum and liver, is rarely assessed because invasive biopsies are needed.

In the present patent application, it is proposed a noninvasive magnetic resonance imaging method for the quantification of hepatic fat content and visceral adipose tissue fatty acid composition in mice on a 7.0 T preclinical system. As demonstrated by the in vitro experiments performed on well calibrated fat-water emulsions, there was a strong agreement between the weight fraction of the dispersed phase in hazelnut oil and the PDFF measured with our method. Second, the number of double bounds ndb and the number of methylene-interrupted double bounds nmidb in vegetable oils were in agreement with the theoretical values calculated using oil composition.

In vivo, significant differences in fatty acid composition of visceral adipose tissue were observed according to the mice diet. In the fructose diet mice, the visceral fat contained significantly more PUFA and less SFA than in the high fat diet mice. Since PUFA cannot be synthetized by lipogenesis, these measurements reflect the composition of the diet, the fructose diet containing two times more PUFA than the high fat diet. This is in agreement with the results of previous studies reporting that the adipose tissue, and more particularly the visceral adipose tissue is a diet biomarker. These results suggest that changes in adipose tissue fatty acid composition reflecting changes in diet can be measured with the presented magnetic resonance imaging method.

To conclude, with the proposed method, it is feasible to quantify both hepatic fat content and visceral adipose tissue fatty acid composition with 7.0T magnetic resonance imaging in mice. The non-invasive determination of visceral fatty acid composition will enable following its evolution according to changes of diet in small animals.

The embodiments and alternative embodiments considered here-above can be combined to generate further embodiments of the invention.

The invention claimed is:

1. A method for post-processing images of a region of interest in a subject, the images being acquired with a magnetic resonance imaging technique, the magnetic resonance imaging technique involving successive echoes of a multiple-gradient echo sequence with bipolar readout gradients, each image associating to each pixel of the image the amplitude of the measured signal in the magnetic resonance imaging technique and the phase of the measured signal in the magnetic resonance imaging technique, the method for post-processing comprising at least the step of:

unwrapping the phase of each image, to obtain unwrapped images, extracting a complex signal over echo time for at least one pixel of the unwrapped images, to obtain at least one extracted complex signal, and calculating fat characterization parameters by using a fitting technique applied on a model, the model being a function which associates to a plurality of parameters each extracted complex signal, the plurality of parameters comprising at least two fat characterization parameters, the magnitude error generated by the use of the bipolar readout gradients and the phase error generated by the use of the bipolar readout gradients, the fitting technique being a non-linear least-square fitting technique using pseudo-random initial conditions.

2. The method for post-processing images according to claim 1, wherein the fat characterization parameters are chosen in the group consisting of the number of double bounds, the number of methylene-interrupted double bounds and the chain length.

3. The method for post-processing images according to claim 1, wherein the method for post-processing images further comprises the step of:

determining the phase jump in the phase between two images, the first image being acquired at a first echo and the second image being acquired at a second consecutive echo, comparing the phase jump with a threshold value, and correcting the phase value when the phase jump is superior or equal to the threshold value.

4. The method for post-processing images according to claim 1, wherein the model further depends on the complex intensity of water, the complex intensity of fat and a complex field map taking into account the effect of transversal relaxivity rate and the field inhomogeneity in the magnetic field used in the magnetic resonance imaging technique.

5. The method for post-processing images according to claim 1, wherein the method for post-processing images further comprises the step of:

quantifying the proportion of unsaturated fatty acids and proportion of saturated fatty acids in the region of interest in the subject based on the calculated fat characterization parameters.

6. The method for post-processing images according to claim 5, wherein the quantifying step comprises determining the proton density fat fraction and the fatty acid composition based on the calculated fat characterization parameters.

7. A method for predicting that a subject is at risk of suffering from an obesity related disease, the method for predicting at least comprising the step of:

carrying out the steps of the method for post-processing images of the subject according to claim 1, to obtain fat characterization parameters, and predicting that the subject is at risk of suffering from the obesity related disease based on the fat characterization parameters.

8. A method for diagnosing an obesity related disease, the method for diagnosing at least comprising the step of:

carrying out the steps of the method for post-processing images of the subject according to claim 1, to obtain fat characterization parameters, and diagnosing the obesity related disease based on the fat characterization parameters.

9. A method for monitoring the responsiveness of a subject suffering from an obesity related disease to a treatment useful for said disease, the method for monitoring the responsiveness comprising:

carrying out the steps of the method for post-processing images of the subject according to claim 1, to obtain fat characterization parameters before the treatment, carrying out the steps of the method for post-processing images of the subject according to claim 1, to obtain fat characterization parameters during or after the treatment, and comparing the fat characterization parameters before the treatment with the fat characterization parameters during or after the treatment, a difference between said fat characterization parameters being indicative that the treatment is effective.

10. A method for screening a probiotic, a prebiotic, a chemical compound or a biological compound suitable for obtaining a treatment useful for an obesity related disease using the method for monitoring the responsiveness of a subject according to claim 9.

11. A method for monitoring the proportion of unsaturated fatty acids and proportion of saturated fatty acids in a region of interest in a subject, the method for monitoring at least comprising the step of:

imaging the region of interest in the subject by using a magnetic resonance imaging technique, the magnetic resonance imaging technique involving successive echoes of a multiple-gradient echo sequence with bipolar readout gradients, to obtain images carrying out the steps of the method for post-processing the obtained images according to claim 1, to obtain fat characterization parameters, and quantifying the proportion of unsaturated fatty acids and proportion of saturated fatty acids in the region of interest in the subject based on the calculated fat characterization parameters.

12. The method for monitoring according to claim 11, wherein the magnetic resonance imaging technique involves using a magnetic field value comprised between 1.0 T and 11.7 T.

13. A method for identifying a biomarker, the biomarker being a diagnostic biomarker of an obesity related disease, a susceptibility biomarker of an obesity related disease, a prognostic biomarker of an obesity related disease or a predictive biomarker in response to the treatment of an obesity related disease, the method comprising the steps of:

carrying out the steps of the method for post-processing images according to claim 1, to obtain first fat characterization parameters from a subject suffering from the obesity related disease, carrying out the steps of the method for post-processing images according to claim 1, to obtain second fat characterization parameters from a subject not suffering from the obesity related disease, and selecting a biomarker based on the comparison of the first and second obtained parameters.

14. A non-transitory computer readable medium having encoded thereon a computer program comprising instructions for carrying out a method of claim 1 when said computer program is executed on a suitable computer device.

15. A device for monitoring the proportion of unsaturated fatty acids and proportion of saturated fatty acids in a region of interest in a subject, the device comprising:

a magnetic resonance imaging system adapted to image the region of interest in the subject by using a magnetic resonance imaging technique, the magnetic resonance imaging technique involving successive echoes of a multiple-gradient echo sequence with bipolar readout gradients, to obtain images and a controller adapted to:

receive the obtained images of the region of interest from the magnetic resonance imaging system, each image associating to each pixel of the image the amplitude of the measured signal in the magnetic resonance imaging technique and the phase of the measured signal in the magnetic resonance imaging technique, unwrap the phase of each image, to obtain unwrapped images, extract a complex signal over echo time for at least one pixel of the unwrapped images, to obtain at least one extracted complex signal, calculate fat characterization parameters by using a fitting technique applied on a model, the model being a function which associates to a plurality of parameters each extracted complex signal, the plurality of parameters comprising at least two fat characterization parameters, the magnitude error generated by the use of the bipolar readout gradients and the phase error generated by the use of the bipolar readout gradients, the fitting technique being a non-linear least-square fitting technique using pseudo-random initial conditions, and quantify the proportion of unsaturated fatty acids and proportion of saturated fatty acids in the region of interest in the subject based on the calculated fat characterization parameters.

16. A device for monitoring according to claim 15, the magnetic resonance imaging system is adapted to apply a magnetic field whose magnetic field value comprised between 1.0 T and 11.7 T.

17. A device for monitoring according to claim 15, the magnetic resonance imaging system is adapted to image a field of view defining a maximum perimeter, the subject having dimensions such that the subject be smaller than the region of interest delimited by the maximum perimeter.

* * * * *